(12) United States Patent
Enriquez-Sarano (10) Patent No.: US 11,896,483 B2
(45) Date of Patent: Feb. 13, 2024

(54) TRANSCATHETER VALVE LEAD AND VALVE ELEMENT

(71) Applicant: Maurice Enriquez-Sarano, Rochester, MN (US)

(72) Inventor: Maurice Enriquez-Sarano, Rochester, MN (US)

(*) Notice: Subject to any disclaimer, the term of this patent is extended or adjusted under 35 U.S.C. 154(b) by 327 days.

(21) Appl. No.: 17/181,703

(22) Filed: Feb. 22, 2021

(65) Prior Publication Data

US 2021/0259830 A1 Aug. 26, 2021

Related U.S. Application Data

(60) Provisional application No. 62/979,043, filed on Feb. 20, 2020.

(51) Int. Cl.
A61F 2/24 (2006.01)

(52) U.S. Cl.
CPC ............ *A61F 2/2418* (2013.01); *A61F 2/246* (2013.01); *A61F 2/2409* (2013.01); *A61F 2/2427* (2013.01); *A61F 2/2454* (2013.01); *A61F 2220/0083* (2013.01)

(58) Field of Classification Search
CPC .... A61F 2/2418; A61F 2/2427; A61F 2/2454; A61F 2/2457; A61F 2/246
See application file for complete search history.

(56) References Cited

U.S. PATENT DOCUMENTS

| | | | |
|---|---|---|---|
| 10,105,226 B2 | 10/2018 | Zimmerman | |
| 10,226,334 B2 | 3/2019 | Rowe et al. | |
| 10,617,520 B2 | 4/2020 | Rowe et al. | |
| 10,952,846 B2 | 3/2021 | Rowe et al. | |
| 2009/0276040 A1 | 11/2009 | Rowe et al. | |
| 2013/0053950 A1 | 2/2013 | Rowe et al. | |
| 2015/0127096 A1 | 5/2015 | Rowe et al. | |
| 2015/0250590 A1* | 9/2015 | Gries | A61B 17/0401 623/2.11 |
| 2017/0143478 A1* | 5/2017 | Schwartz | A61F 2/2412 |
| 2017/0172737 A1 | 6/2017 | Kuetting et al. | |
| 2017/0348098 A1 | 12/2017 | Rowe et al. | |
| 2018/0289473 A1* | 10/2018 | Rajagopal | A61F 2/2427 |
| 2019/0015205 A1 | 1/2019 | Rajagopal et al. | |
| 2019/0133761 A1 | 5/2019 | Rowe et al. | |
| 2019/0290431 A1* | 9/2019 | Genovese | A61F 2/2466 |
| 2021/0196457 A1 | 7/2021 | Rowe et al. | |

FOREIGN PATENT DOCUMENTS

EP 3 050 541 B1 8/2019

OTHER PUBLICATIONS

International Search Report and Written Opinion for International Application No. PCT/US2021/019040, dated Aug. 17, 2021, 18 pages.

* cited by examiner

*Primary Examiner* — Suba Ganesan
(74) *Attorney, Agent, or Firm* — Westman, Champlin & Koehler, P.A.

(57) ABSTRACT

A cardiac valve delivery system includes a lead configured to be inserted through a venous system to a heart, the lead having a distal end with a myocardial attachment apparatus, and a transcatheter prosthesis element configured to be delivered along the lead. The transcatheter prosthesis is configured with an anchoring element located on the outside rim of the prosthesis, configured to fix the transcatheter prosthesis in place along the lead. The prosthesis is also movable along the lead and steerable towards the appropriate angulation with the lead.

16 Claims, 10 Drawing Sheets

TRANSCATHETER VALVE LEAD AND VALVE ELEMENT

CROSS-REFERENCE TO RELATED APPLICATION

The present application is based on and claims the benefit of U.S. provisional patent application Serial No. 62/979,043, filed Feb. 20, 2020, the content of which is hereby incorporated by reference in its entirety.

FIELD

This disclosure is directed toward atrioventricular transcatheter valve replacement, and particularly, to transcatheter tricuspid valve replacement for tricuspid valve regurgitation.

BACKGROUND

When a valve in a human heart is damaged or diseased, or the heart itself is damaged or diseased, some backflow through the one-way valves may occur. This is known as valve regurgitation. Continued regurgitation can lead to further weakening of the valve, and increased difficulty in operation of the heart muscles, and can lead to heart failure, cardiac morbid complications and ultimately death. Transcatheter treatment of damaged valves such as the aortic valve have been used, which insert replacement valves and deploy those into calcified areas of the damaged valve, for the purpose of anchoring the prosthesis while opening the damaged valve. However, there is little to no calcification or firm anchor area in the vicinity of the atrioventricular valves particularly the tricuspid valve. Percutaneous repair of the damaged valve using stitching or other adherence devices is particularly difficult due to the weakness of the valvular tissue or myocardium in the atrioventricular region particularly the Tricuspid area. Therefore, replacement valves or repaired valves do not have the proper backing with which they may be adhered or anchored.

Accordingly, atrioventricular valve repair and replacement, particularly tricuspid, are difficult and less effective than other valve repair and/or replacement and are prone to marked residual regurgitation and failure. Further, atrioventricular valve apparatus, particularly the tricuspid valve have thin tissue and the valve and surrounding annular and myocardial tissue are weak and subject to tearing. Still further, the ventricular and atrial myocardium is thinner in the right than in the left side of the heart, further increasing the difficulty of repair and/or replacement of the tricuspid valve and yield devices that are prone to tearing the heart muscle leading to rupture or death.

It is estimated that over 3.5 million patients are affected by mitral valve regurgitation and that 1.6 million patients are affected with tricuspid valve regurgitation in the US and that more than 80% go untreated during their lifetime. This translates into an incidence of 350,000 to 400,000 new patients affected by mitral regurgitation and 160,000 to 240,000 new patients affected by tricuspid regurgitation every year. One reason for the failure to treat patients with mitral or tricuspid valve conditions, is the high risk of surgical intervention with poor tolerance to cardiopulmonary bypass and the frequent failures of surgical treatment. Thus, recent data have demonstrated that patients with mitral or tricuspid regurgitation incur a considerable excess mortality after they are diagnosed with the disease.

The most common cause of tricuspid regurgitation is functional (with structurally normal leaflets) with enlargement of the tricuspid annulus or right ventricle, often due to other heart or lung disorders, such as mitral valve diseases, heart failure or pulmonary hypertension. These conditions induce excessive valvular tenting and annular enlargement resulting in separation of the tricuspid leaflets which can't close completely.

Tricuspid valve regurgitation may also be caused by organic valve disease (structurally abnormal leaflets) such as congenital heart disease (including Ebstein anomaly), injury, infection of the heart valves (infective endocarditis) associated with the use of illicit drugs, chemical toxicity (Carcinoid, ergot), post-inflammatory disease (rheumatic fever), or iatrogenic (pace-maker, biopsy).

The approved treatment of tricuspid regurgitation is surgical valve repair or replacement, but this approach is hindered by high operative mortality, frequent recurrence of the regurgitation and is rarely used. In regard to transcatheter techniques for treatment of tricuspid regurgitation, the tricuspid valve has a complex anatomy not prone to easy repair, and does not have a calcium buildup, and therefore provides no reasonable anchor location to hold an implanted prosthetic valve. Furthermore, the fragile nature of the tricuspid leaflets and annulus and of the right ventricular myocardium, safe implantation and anchoring of treatments such as tricuspid valve replacement or repair, are very difficult.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

In one embodiment, a cardiac valve delivery system includes a lead configured to be inserted through a venous system to a heart, the lead having a distal end with a myocardial attachment apparatus, and a transcatheter prosthesis element configured to be delivered along the lead. The transcatheter prosthesis is configured with an anchoring element located on the outside rim of the prosthesis, configured to fix the transcatheter prosthesis in place along the lead. The prosthesis is also movable along the lead and steerable towards the appropriate angulation with the lead.

In various additional features of the embodiment, the myocardial attachment apparatus includes a screw deployable at an angle of substantially 90 degrees from a longitudinal axis of the distal end. The screw in one embodiment comprises a mesh deployable from a distal end thereto, the mesh configured to anchor through heart tissue. The myocardial attachment of the lead may be formed by hooks or deployable struts through the ventricular septum and/or the right ventricular myocardium. The transcatheter prosthesis may comprise a prosthesis mesh crimpable to contain a crimped valve element deliverable along the lead.

In one embodiment, the anchoring element includes a central immobile element attached to the prosthesis mesh, and a pair of articulated semi-cylindrical wings movably coupled to the central immobile element. The pair of wings is movable between a delivery position in which the wings do not engage the lead, and an anchoring position in which the wings are closed in embrace over the lead to anchor the transcatheter prosthesis to the lead. The anchoring element may comprise a loop attached to the prosthesis mesh and around the lead.

In another feature, the prosthesis mesh is conical in shape when uncrimped, with a first opening at a ventricular opening, and a second opening, larger than the first opening, and is configured to be deployed intra-atrially at anchoring.

In another feature, the transcatheter prosthesis is configured to allow existing valvular tissue in the heart to rest on top of an external side of the prosthesis mesh.

The various features may be combined with one another in various combinations.

In another embodiment, a transcatheter prosthesis includes a prosthesis mesh crimpable to contain a crimped valve element deliverable along a lead, and an anchoring element configured to fix the transcatheter prosthesis in place along the lead. The transcatheter prosthesis is configurable to be delivered intravenously to a heart along a lead by the anchoring element.

In another feature, the anchoring element further comprises a central immobile element attached to the prosthesis mesh, and a pair of articulated semi-cylindrical wings movably coupled to the central immobile element. The pair of wings is movable between a delivery position in which the wings do not engage the lead, and an anchoring position in which the wings are closed in embrace over the lead to anchor the transcatheter prosthesis to the lead.

The various features may be combined with one another in various combinations.

This summary is not intended to describe each disclosed embodiment or every implementation of transcatheter valve leads and valve elements as described herein. Many other novel advantages, features, and relationships will become apparent as this description proceeds. The figures and the description that follow more particularly exemplify illustrative embodiments

DETAILED DESCRIPTION

The present disclosure relates generally to a system of transcatheter treatment of tricuspid valve regurgitation. The system involves implantation of a supporting and guiding lead attached to the right side of the heart, in one embodiment at the apical or middle ventricular septum but associated various other locations can be used to complement this implantation site. The lead is inserted in one embodiment via the systemic venous system through the left or right subclavian veins and the superior vena cava. Alternative approaches using initial inferior vena cava approach with lasso capture from the superior vena cava can be considered in other embodiments. The lead attachment to the ventricular septal myocardium is secured in one embodiment using one screw or multiple screws implantation into the ventricular myocardium, preferentially the ventricular septum, and involving in some embodiments, the deployment of a supportive mesh (or hooks, metallic rods or scalloped devices in other embodiments) on the left side of the ventricular septum. The screw is carried in one embodiment at an end of the lead and post-implantation the lead is rotated to remain perpendicular to the implanted screw.

The lead may be formed in some embodiments of a wider portion at the tricuspid annular or valvular level that contains an elastic hysteresis system providing elastic support to the prosthetic position. After lead implantation and secure attachment to the ventricular myocardium, the lead serves as a guide to slide a crimped prosthesis introduced through the same venous approach.

In one embodiment, a guiding system is formed by an anchor attached to the external wall of the crimped prosthesis and carrying a ring, loop or approximated wings that allow the prosthesis to slide crimped on the lead and external to the body of the prosthesis. The crimped prosthesis is thus guided through the superior vena cava and right atrium, up to the tricuspid valve. The prosthesis is then moved to the appropriate position between the tricuspid valve leaflets. When the position is judged adequate the prosthesis is anchored on the lead through tightening of the winged system (or loop or annular guiding system) attached to the anchor on the external side of the crimped prosthesis over the implanted lead. The crimped prosthesis is then deployed and covered on its side by the remnants of the existing tricuspid valve tissue.

In some embodiments, the prosthesis is steerable using a rotating anchor system allowing a practitioner to direct the prosthesis towards the septal or inferior walls of the ventricle. The implanted prosthesis is made in one embodiment of a nitinol mesh covered in some embodiments by a skirt and in some embodiments of cono-truncal shape. The leaflets of a replacement valvular prosthesis implanted in the nitinol shape may be made of human, equine, porcine, or bovine tissue or artificial fabric. The external positioning of the anchoring system ensures coaptation without interference of a lead through the prosthesis.

Figure 1A:
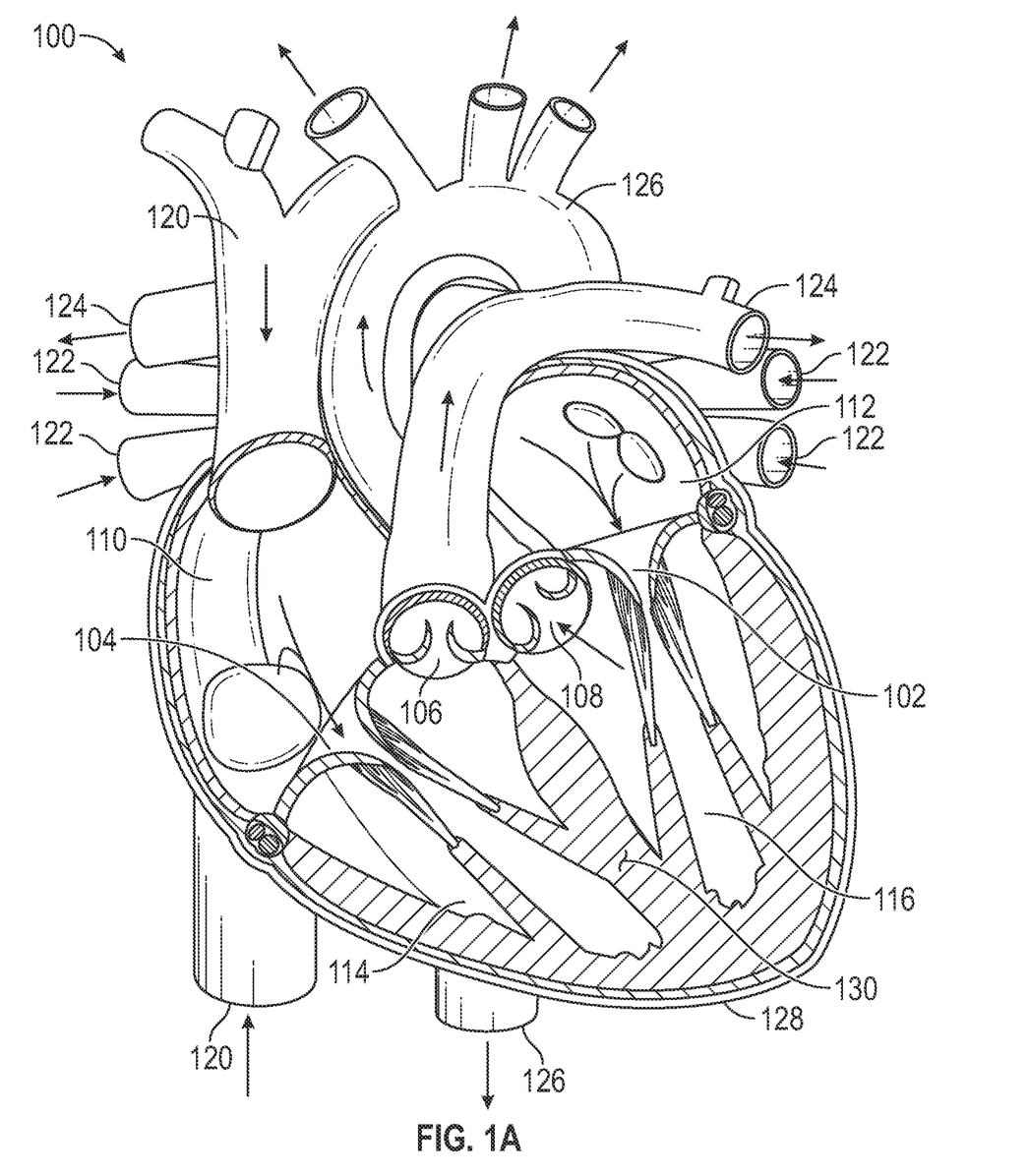
FIG. 1A is a partial front cutaway view of a human heart.
Figure 1B:
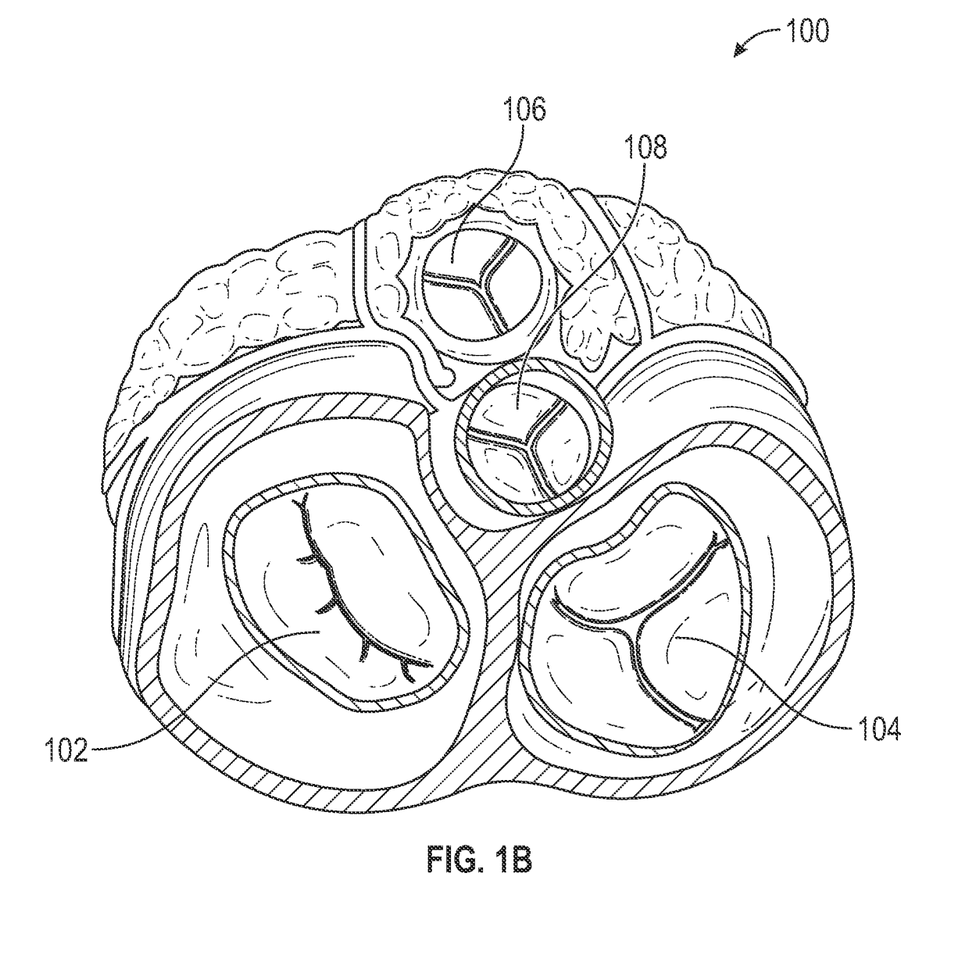
FIG. 1B is a partial rear cutaway view of a portion of a human heart.

FIGS. 1A and 1B show a front section view (FIG. 1A) and a back-section view (FIG. 1B) of a heart 100. FIGS. 1A and 1B show partial detail of atrioventricular valves (including mitral valve 102, tricuspid valve 104, pulmonary valve 106, and aortic valve 108) and their operation. The atrioventricular valves in the heart operate to control blood flow into and out of the atria (right atrium 110 and left atrium 112) and the ventricles (right ventricle 114 and left ventricle 116). The bicuspid (or mitral) valve 102 regulates blood flow from the left atrium 112 into the left ventricle 116, and in normal operation prevents blood flow from the left ventricle 116 back into the left atrium 112. The tricuspid valve 104 regulates blood flow from the right atrium 110 into the right ventricle 114, and in normal operation prevents blood flow from the right ventricle 114 back into the right atrium 110. When the valves 102, 104 are healthy and properly operating, they act as one way valves. Veins 120 in the body supply non-oxygenated blood into the right atrium 110 of the heart, and veins 122 supply oxygenated blood from the lungs. Arteries provide a pathway from the heart to the body, pulmonary arteries 124 from the right ventricle 114 to the lungs, and the aorta 126 from the left ventricle 114 to the rest of the body.

Referring also to FIG. 1A, the tricuspid valve 104 separates the right atrium 110 and right ventricle 114. Venous access particularly through the superior vena cava 120 provides direct access to the right atrium and ventricle and the tricuspid valve. Note the much thinner wall of the right ventricle 114 versus the left ventricle 116.

Referring also to FIG. 1B, the normal tricuspid valve is well seen on the right side with its 3 leaflets. In cases of tricuspid regurgitation, the leaflets show incomplete coaptation in systole causing the regurgitation.

When the heart 100 pumps, blood is pumped into the atria (right 110 and left 112) of the heart 100, and out of the ventricles (via pulmonary valve 106 and aortic valve 108), exiting the right 114 and left 116 ventricles. Upon contraction of the right atrium 110, blood collected in the right atrium 110 is forced through the tricuspid valve 104 into the right ventricle 114. At the same time, the left atrium 112 contracts and blood from that has collected in the left atrium 112 is forced through the mitral valve 102 into the left ventricle 116. Then, the right ventricle 114 and left ventricle 116 contract, forcing blood in the right ventricle 114 and left ventricle 116 through the pulmonary valve 106 and the aortic valve 108, respectively, to the pulmonary artery 124 and aorta 126. Pericardium, or heart wall, 128 is the exterior sheath of the heart. Ventricular septum 130 separates the right ventricle 114 and the left ventricle 116. Normally operating valves allow blood flow in one direction.

Figure 2:
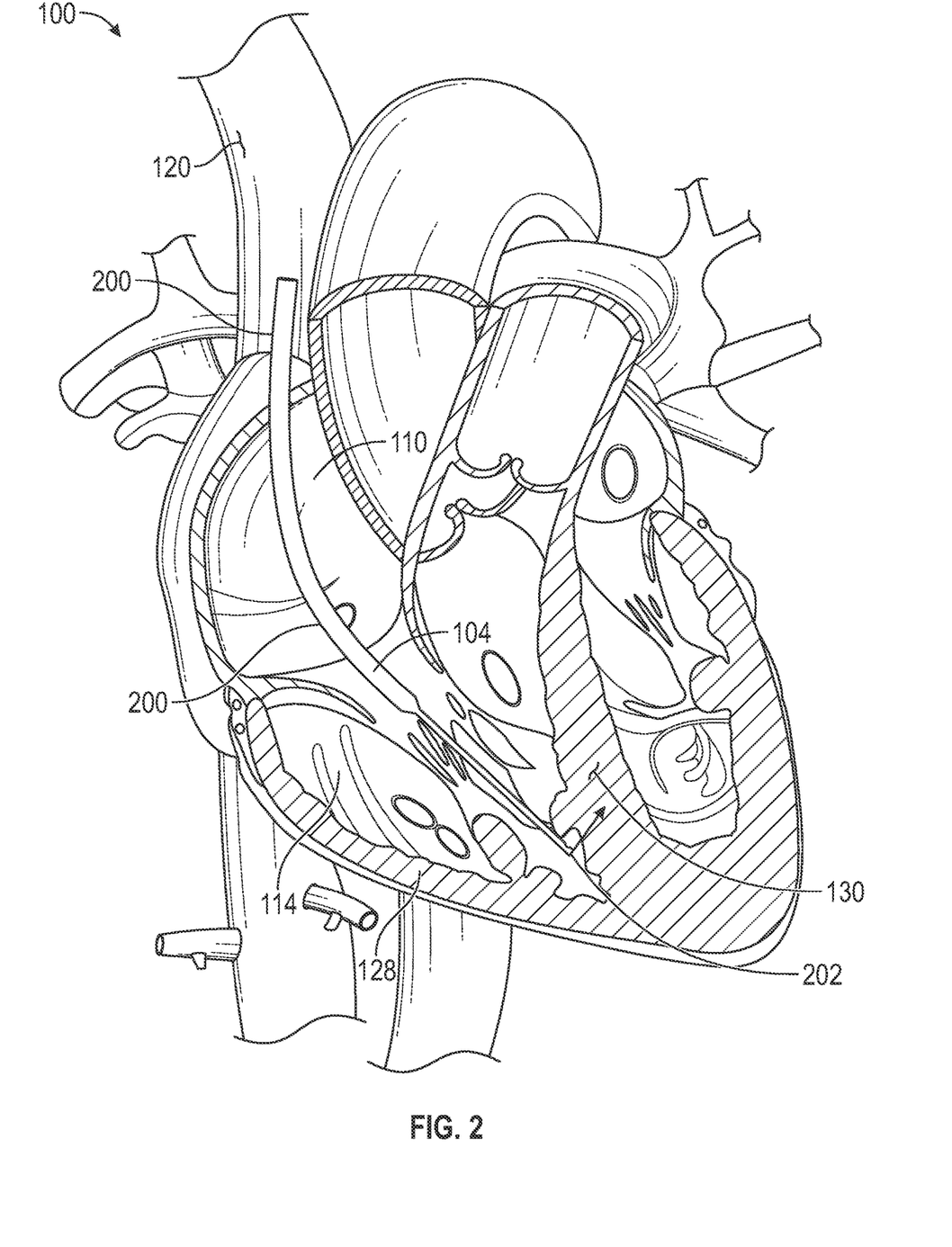
FIG. 2 is a partial cutaway view of a human heart showing an embodiment of the present disclosure therein.

FIG. 2 shows a diagram of insertion of a lead 200 inserted via the superior vena cava 120 into the right atrium 110, through the tricuspid valve 104, and into the right ventricle 114. Such an introduction and placement of the lead 200 allows for later replacement and/or repair of the tricuspid valve 104. This transcatheter insertion of lead 200 results in one embodiment in the lead 200 having an end 202 positioned within the right ventricle 114 in contact to the ventricular septum 130. The lead 200 in one embodiment guides and supports the transcatheter prosthesis The catheter lead 200 is introduced through the superior vena cava 120 and advanced through right atrium 110 and the right ventricle 114 to be put in close contact with the ventricular septum 130. In other embodiments the lead 200 can be introduced through the inferior vena cava and captured by a lasso introduced through the superior vena cava 120.

Figure 3:
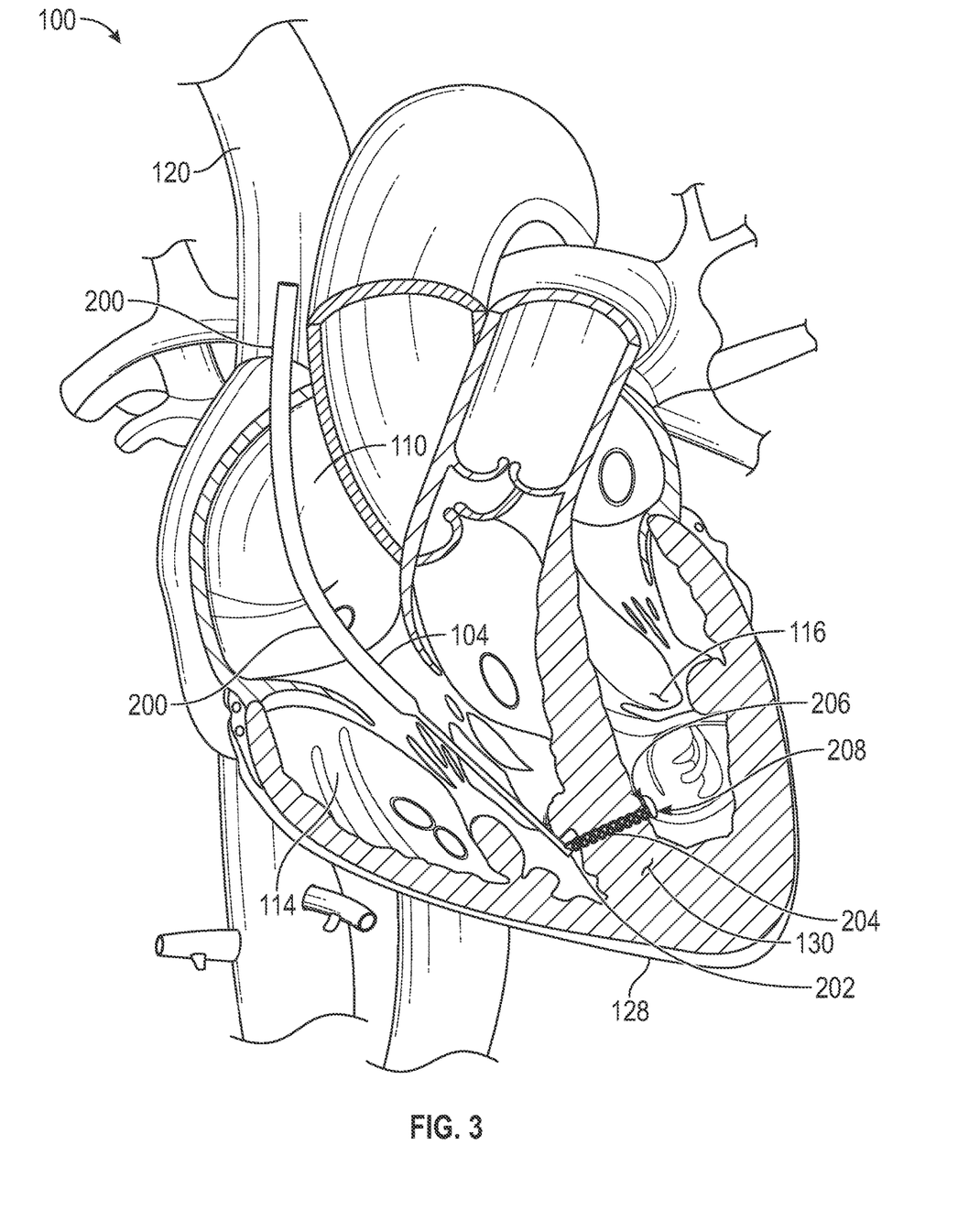
FIG. 3 is a partial cutaway view of a human heart showing another embodiment of the present disclosure therein.

FIG. 3 shows the view of FIG. 2 wherein the end 202 of lead 200 has a screw 204 deployed thereon. The screw 204 screws into and attaches to the apical portion of the ventricular septum 130. In one embodiment, an end 206 of the screw 204 that extends into the apical ventricular septum 130 carries a mesh 208 that is deployed from the screw 204 to provide a backing on the left ventricle 116 side of the apical ventricular septum.

The head of the catheter 202 is apposed against the ventricular septum 130. This positioning allows the introduction of a screw 204 attached to the head of the catheter/lead into the ventricular septum 130 to securely attach the lead 200 to the ventricular septum 130. In other embodiments, other methods of attachment of the lead to the ventricular septum 130 can be used, such as hooks, metallic rods or scalloped devices used to secure the attachment of the lead 200 to the septum 130. Deployment of a mesh 208 on the left ventricular side of the septum from the tip 206 of the screw 204 may additionally secure the attachment. In other embodiments the mesh 208 can be replaced by any type of constraint device that will hold the left side of the ventricular septum 130 to avoid slippage of the septal attachment device or tearing of the myocardium.

Figure 4:
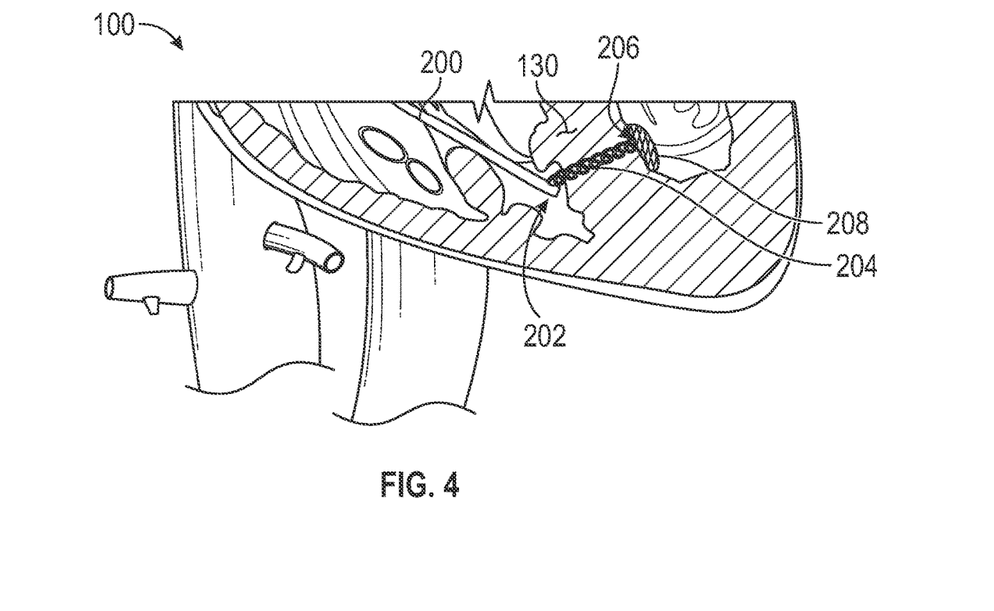
FIG. 4 is a close-up view of a portion of the heart showing the embodiment of FIG. 3.

FIG. 4 is an enlarged view of a portion of the heart 100 of FIG. 3 showing the lead 200, end 202, screw 204 with end 206, and mesh 208. The tip of the lead 202 is seen closely apposed to the right side of the ventricular septum 130 and delivering an attachment device, screw as shown 204, or any other embodiment, with a potential material for contention of the left side of the septum, mesh as shown 208, or other embodiments of septal contention devices.

Figure 5:
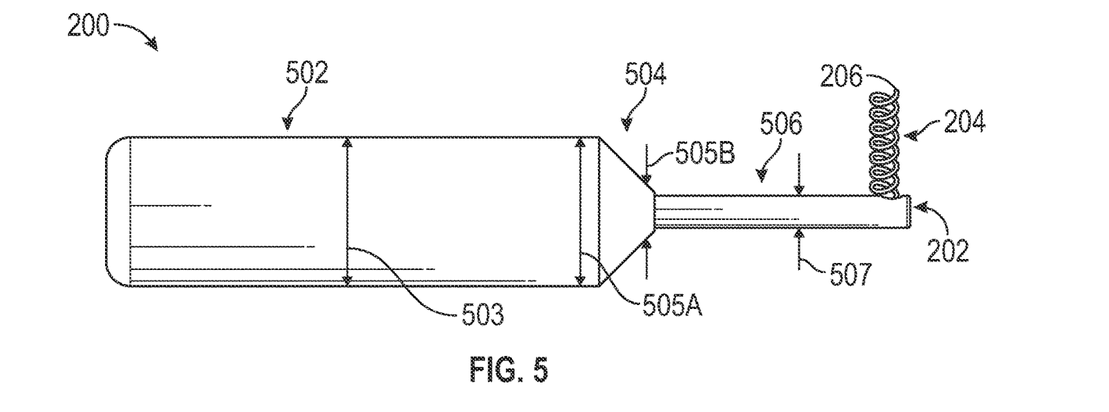
FIG. 5 is a diagram of a portion of a lead according to an embodiment of the present disclosure.

FIG. 5 is a diagram showing one embodiment of lead 200. Near end 202 of lead 200, where screw 504 is positioned, a proximal part 502 of the lead having a first diameter 503 that in one embodiment is substantially the same as that of a main body of the lead 200, a medium part 504 of the lead 200 having a diameter that varies between the proximal part 502 and a distal part 506 from diameter 505A to diameter 505B. This medium part 504 allows for hysteresis elongation of an elastic system. Distal part 506 of the lead 200 has a diameter 507 smaller than the first diameter 503 and houses the screw 204 for myocardial implantation, such as in the ventricular septum 130 as described elsewhere herein.

The screw 204 is used for implantation into, for example, the apical ventricular septum 130, to anchor the lead for placement of a replacement tricuspid valve in one embodiment. While diameter is described with respect to a lead 200 that is tubular, it should be understood that the lead 200 may have different cross sectional shaping, such as substantially tubular, oval, or the like. Those of skill in the art will recognize that any cardiac catheter through which the lead may be inserted is amenable for use with embodiments of the present disclosure.

The intracardiac part of the lead 200 is schematically presented with three parts: the distal part (tip 507) of the lead 202 carries the myocardial attachment device (screw 204 or other embodiment). In other embodiment of this part of the lead, the myocardial attachment (screw or other) is positioned at the exact tip in the direction of the lead for myocardial insertion and rotates to assume an angle (closest to 90°) to ensure traction forces perpendicular to the myocardial insertion. The tip 206 of screw 204 or other type of myocardial insertion in other embodiments allows deployment of myocardial contention on the left side of the ventricular septum. The middle/medium part of the lead 505 A-B continues the distal part of the lead and contains a mechanism of hysteresis to dampen the traction exerted by the prosthetic valve during systole. The mechanism of hysteresis can be formed by springs, hydraulic systems, solenoid or other electrical system, or any other embodiment that dampens the traction forces. The proximal part of the lead 503 is aimed at anchoring the transcatheter prosthesis and is enlarged so that the grip of the prosthetic anchoring is more secure.

In one embodiment, a portion of the lead 200 includes a damper element configured to dampen forces pushing the prosthesis posteriorly during systole of the heart. Such a damper element may be, by way of example only and not by way of limitation, one of an elastic element formed by springs, fluid, a semisolid buffer, or a loop of the lead.

Figure 6A:
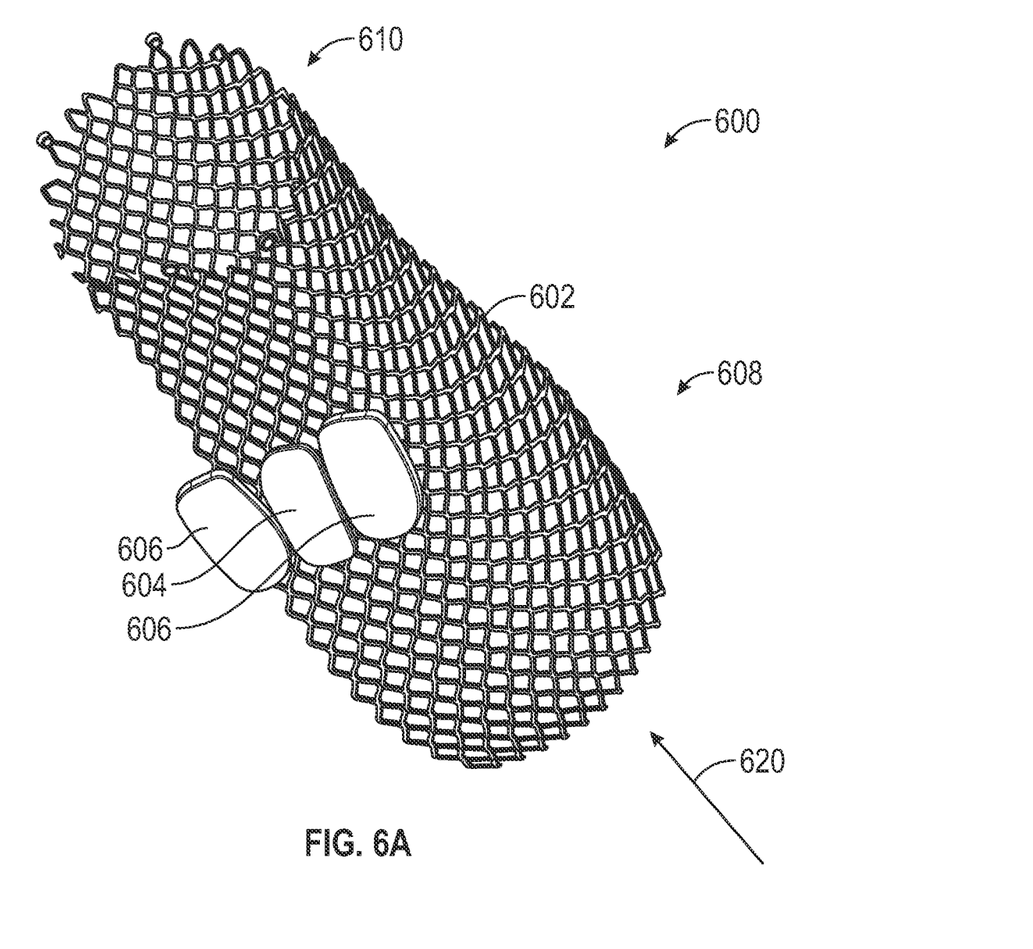
FIG. 6A is a perspective view of an expanded valve element according to an embodiment of the present disclosure.

FIG. 6A is a view of an expanded valve element 600 which may be delivered via a transcatheter approach on the lead 200 as shown above. Valve element 600 includes a frame 602 with an attached anchor 604. Anchor 604 has wings 606 at opposite lateral edges thereof. In one embodiment, frame 602 comprises a conical frame constructed of nickel titanium (e.g., nitinol) and a valvular prosthesis such as a tissue valve of equine, ovine, bovine, porcine, or human tissue, or of an artificial material. The properties of nitinol are known, and their uses in valve repair and/or replacement are also known. The nitinol frame 602 has attached thereto on an external portion thereof an anchor 604. Anchor 604 is used to carry the nitinol frame 602 and a tissue or other valvular prosthesis as the frame comprising and/or containing the valvular prosthesis, and is introduced via the lead 200. In one embodiment, a pair of wings 606 are attached laterally to the anchor 604, a wing 606 on each side of the anchor 604. The valve element 600 is introduced into the heart along the lead 200 with the frame 602 in a compressed form, and is expanded when it is properly aligned with the area of the valve to be replaced/repaired. Nitinol frame 602 is expanded once it is properly placed within the heart, as will be shown below. The valve element 600 is shown in FIG. 6A as a valve repair/replacement for the tricuspid valve between the right atrium 110 and the right ventricle 114. Blood flow from the atrium 110 to the ventricle 114 is shown as moving in the direction of arrow 620. The expanded nitinol frame 602 is in one embodiment conical in shape, having a larger cross sectional area 608 at the valve and tapering toward the right ventricle 114.

The transcatheter prosthesis 600 is presented in FIG. 6A in an oblique view showing the right ventricular opening on top. It is formed by a mesh of metal (Nitinol or other) that provides a conical shape 602 once deployed. The ventricular opening is the smallest orifice of the truncated cone 610 and the base of the truncated cone 608 is deployed to be intra-atrial at anchoring. The leaflets of the valve replacement/repair are located inside the metal mesh and can be formed by equine, bovine or porcine tissue, or artificial fabric in various embodiments. Various embodiments involve the existence of skirts covering the external face of the external face of the metal mesh supporting the leaflets. The anchoring mechanism 604 is located and attached to the external face of the metallic mesh. The anchoring mechanism 604 as displayed involves a central immobile element attached to the metallic mesh to which are attached two articulated semi-cylindrical wings 606 that, during implantation, are closed in embrace over the lead 200 to anchor the prosthesis to the lead 200. These wings 606 are semi closed over the lead 200 during the venous insertion of the crimped prosthesis in the venous introducer to providence guidance to the prosthesis to the tricuspid orifice over the lead 200. In other embodiments the anchoring mechanism is formed by a loop attached to the prosthetic anchor. The loop is placed around the lead and introduced with the prosthesis and allows guidance to the proper positioning and then anchoring by tightening the loop over the lead. The shape of the prosthesis is aimed at allowing the existing valvular tissue to rest on top of the external side of the prosthetic cone to prevent periprosthetic regurgitation. Hence this anchoring process allows to leave the leaflets free of intra-prosthetic interaction and allow tailoring the positioning of the prosthesis to avoid excess intra-ventricular protrusion.

Figure 6B:
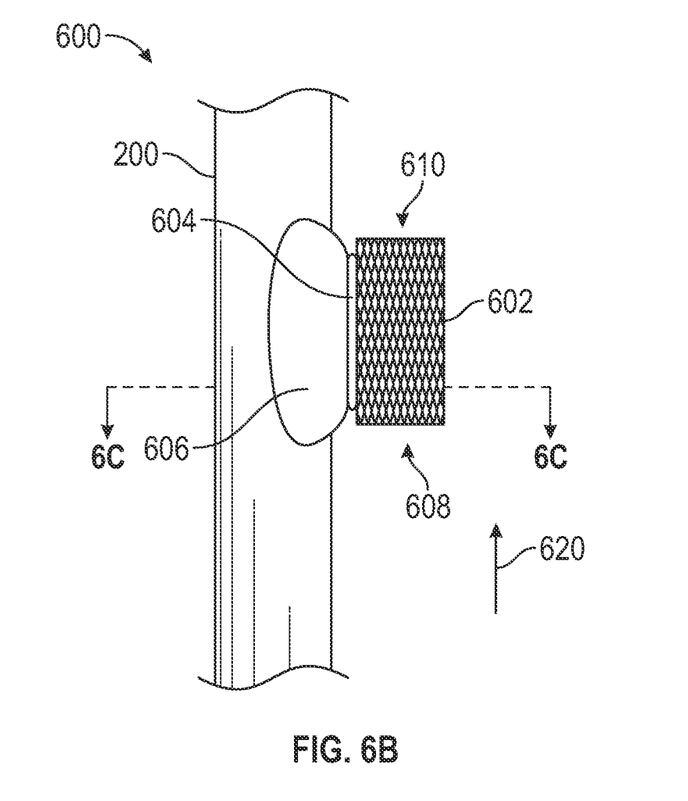
FIG. 6B is a side elevation view of a crimped valve element according to an embodiment of the present disclosure.

FIG. 6B is a side view of the valve element 600 of FIG. 6A showing an unexpanded nitinol frame 602 containing a valvular prosthesis, the anchor 604 to which the frame 602 is mounted or otherwise attached, and the curved wings 606 that may be wrapped around the lead 200 for introduction of the valve element 600 along the lead into the body.

The view of FIG. 6B is from a lateral position to the anchoring mechanism showing the interaction of the lead 200 with the anchoring mechanism. The lead is oriented horizontally with the right ventricle 114 to the right and the right atrium 110 to the left. At the bottom is shown the mesh of the prosthesis 610 with the central anchor 604 attached to the mesh. One semi-cylindrical wing 606 is visible embracing and anchoring the lead 200. In other embodiments, the anchor 604 is attached to a loop that surrounds the lead, allows the prosthesis to slide along the lead and can be tightened around the lead to ensure complete fixation of the anchoring.

Figure 6C:
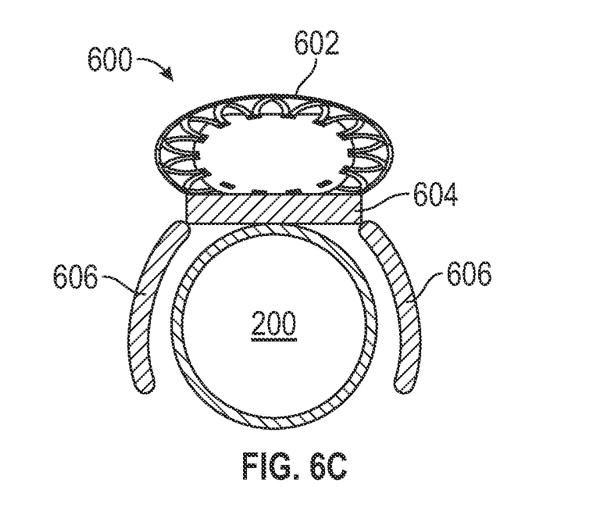
FIG. 6C is a transverse view of the crimped valve element of FIG. 6B taken along lines 6C-6C thereof.

FIG. 6C is a view of the valve element 600 and lead 200 of FIG. 6B taken along lines 6C-6C. FIG. 6C shows the wings 606 wrapping around the lead 200 for clamping thereto when the valve element 600 is properly in position within the heart. In this view the crimped Prosthesis is seen on top of the anchor 604 to which are attached the two semi-cylindrical wings 606 embracing the lead 200.

Figure 6D:
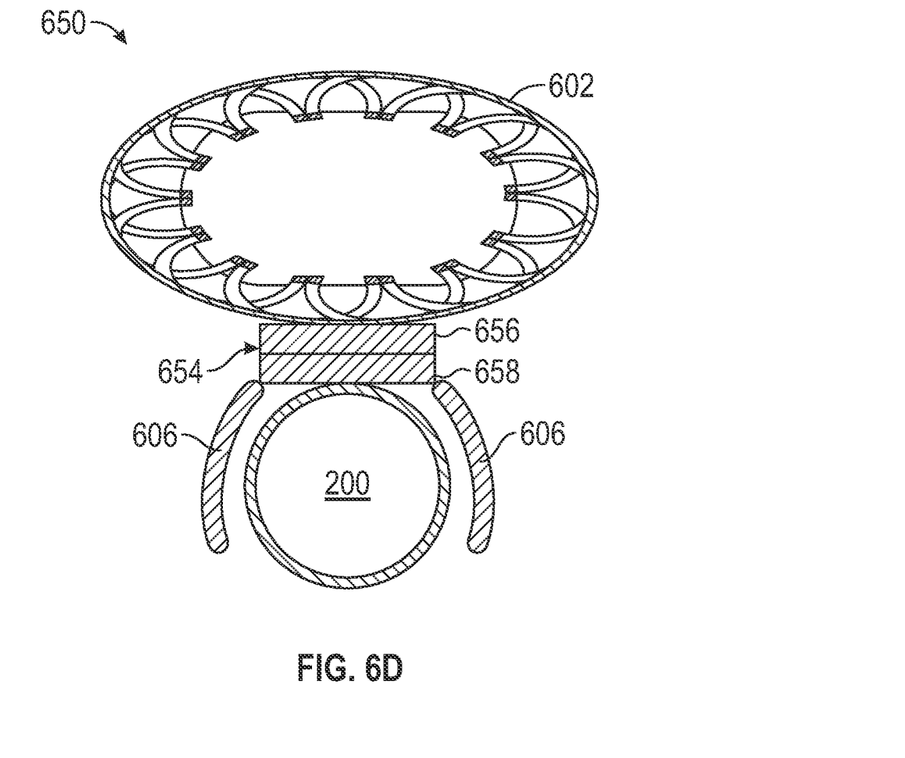
FIG. 6D is a top view of the opened valve element according to another embodiment of the present disclosure.

FIG. 6D is a view of another valve element embodiment 650. In valve element 650, the nitinol frame 602 and valvular prosthesis it contains are that sane as valve element 600. Wings 606 of valve element 650 are the same as wings 606 of valve element 600. However, anchor 604 is replaced with anchor 654 which allows the valve element 650 to be steered or rotated in order to improve the ability of the valve element 654 to be placed properly in position in the heart. Specifically, the anchor 654 is steerable using a rotating system allowing direction of the valve element frame 602 towards the septal or inferior walls of the ventricle. Anchor 654 comprises two anchor components, and upper anchor 656 and a lower anchor 658. The upper anchor 656 and lower anchor 658 are movable with respect to one another in order to allow steerability and to allow proper positioning of the valve element 650 within the heart.

This transverse view shows the anchor in two articulated parts (superior 656 attached to the prosthetic mesh—inferior 658 attached to the semi-cylindrical wings 606 directing and anchoring the prosthesis to the lead-200). This embodiment allows to direct by rotation the deployed prosthesis appropriately towards the septum to minimize the ventricular interaction of the prosthesis and proper valvular interaction, to minimize periprosthetic regurgitation. The two semi-cylindrical wings are shown 606 surrounding the lead 200.

While curved wings 606 have been shown, it should be understood that a different structure for guiding the valve element 600 to the area of the tricuspid valve 104 (or other valve) may be used without departing from the scope of the disclosure. By way of example only and not by way of limitation, a valve element 670 shown in FIG. 6E comprises a ring 672 in place of wings 606. Ring 672, like wings 606, may be cinched or crimped so as to fix its position along the lead 200.

Figure 6E:
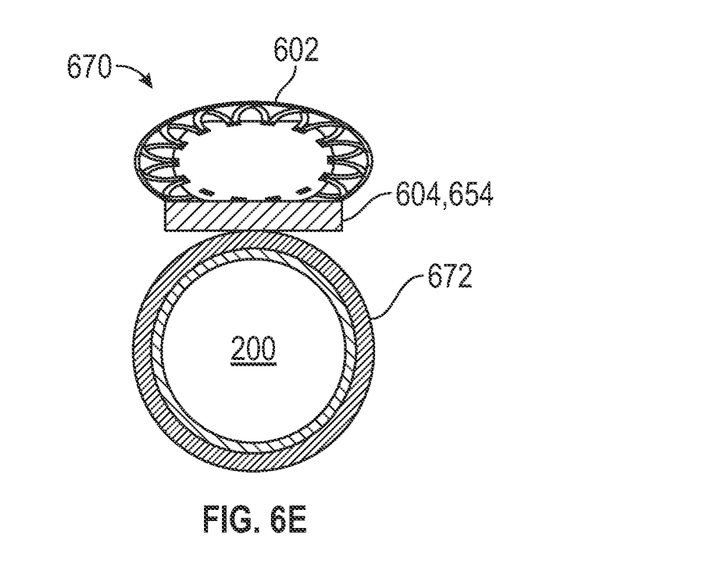
FIG. 6E is a view of an alternative clamping process of the valve element of FIG. 6C.

In this transverse view, FIG. 6E shows the anchoring mechanism involves a loop that, once the valve is in proper position (guided by the loop around the lead), is tightened around the lead to ensure proper anchoring.

Figure 7:
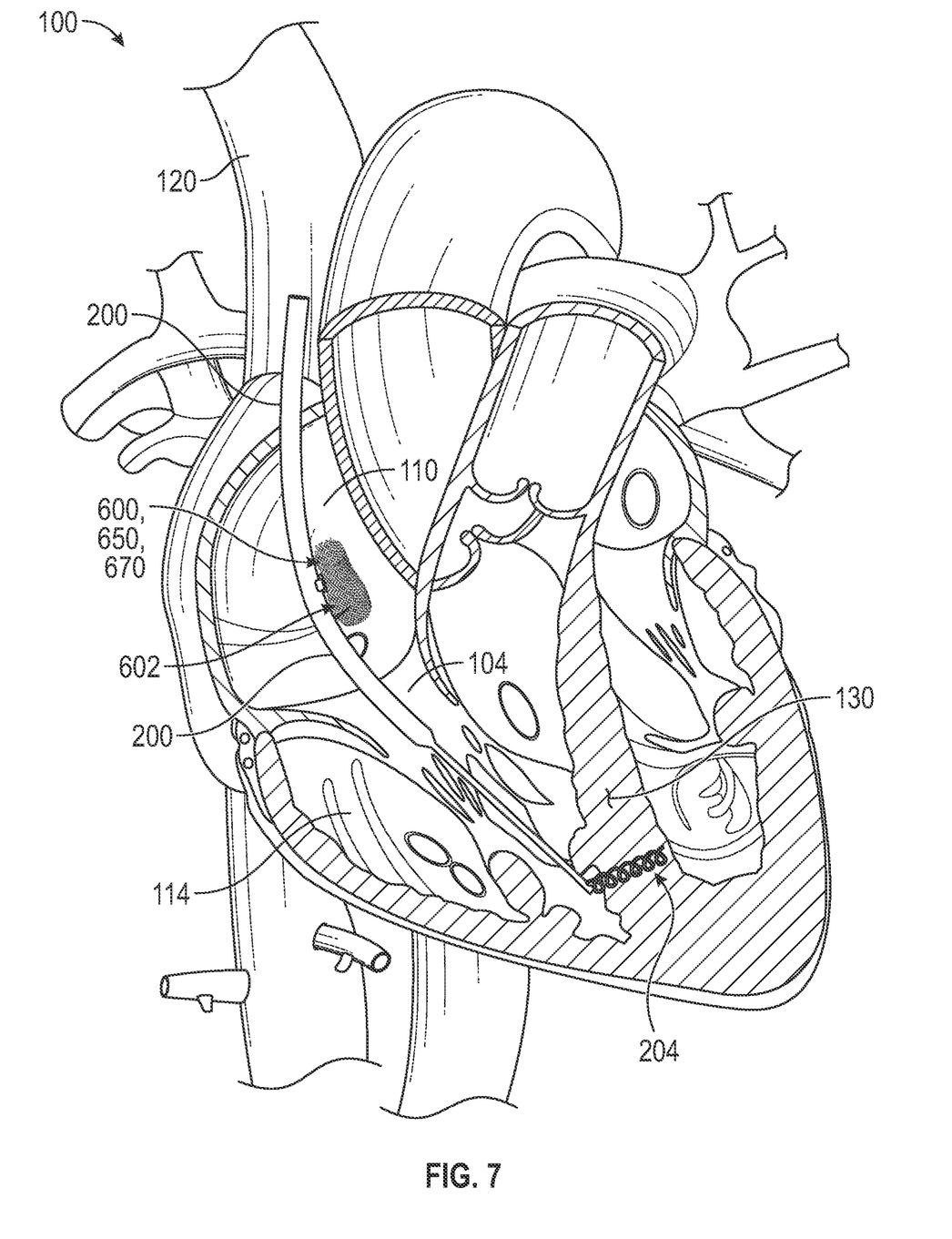
FIG. 7 is a partial cutaway view of a heart on which an embodiment of a crimped valve element is being introduced along a lead according to an embodiment of the present disclosure.

FIG. 7 is a cutaway diagram of a heart 100 into which a lead 200 has been anchored by screw 204 into ventricular septum 130. In operation, implantation of lead 200 is performed as described above, in one embodiment through the superior vena cava into the right atrium 110, through the tricuspid valve 104, into the right ventricle 114, and attached to the ventricular septum 130 with screw 204 in an orientation substantially perpendicular to the insertion orientation of the lead 200. Accordingly, any pull or tension on the lead 200 along its longitudinal axis, which is the most likely pull or tension direction, is substantially perpendicular to the anchor, and less likely than a parallel anchor to be pulled out or otherwise moved or dislodged. As shown, a valve element 600, 650, 670 is being introduced along lead 200 toward the tricuspid valve region. The valve element 600, 650, 670 is shown with crimped or compressed form for ease in introduction through a vein such as the superior vena cava 120.

In operation, implantation of lead 200 is performed as described above, in one embodiment through the superior vena cava into the right atrium 110, through the tricuspid valve 104, into the right ventricle 114, and attached to the ventricular septum 130 with screw 204 in an orientation substantially perpendicular to the insertion orientation of the lead 200. Accordingly, any pull or tension on the lead 200 along its longitudinal axis, which is the most likely pull or tension direction, is substantially perpendicular to the anchor, and less likely than a parallel anchor to be pulled out or otherwise moved or dislodged.

The crimped prosthesis 600, 650, 670 is attached to the previously inserted lead 200 which is secured by the ventricular septal 130 screw 204 initial insertion The attachment allows sliding on the lead 200, ensured by the incompletely closed anchor (loop or semi-cylindrical wings) around the lead 200. The lead 200 guides the crimped prosthesis through the superior vena cava 120 and the prosthesis is seen after progression into the right atrium 110.

Figure 8:
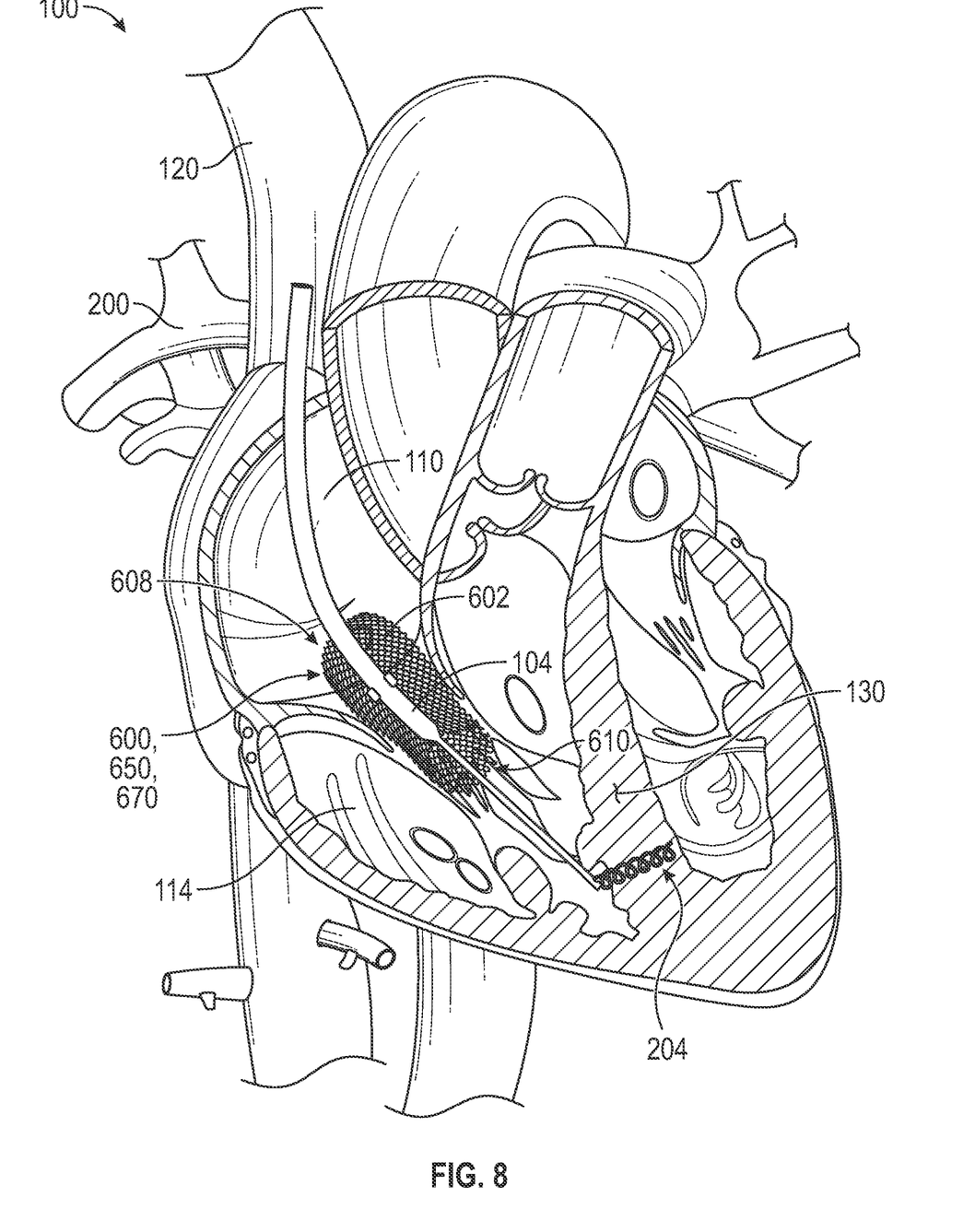
FIG. 8 is a post-expansion view of the valve prosthesis of FIG. 7 in an appropriately positioned location.

FIG. 8 is a cutaway diagram of a heart 100 into which a lead 200 has been anchored by screw 204 into ventricular septum 130. Once the valve element 600, 650, 670 is in proper position with respect to the tricuspid valve 104, the valve element nitinol frame 602 is expanded, and any adjustments that are to be made for proper placement of the valvular prosthesis are made. Once this is performed, the wings 606 or ring 674 are cinched or crimped to the lead 200 to fix the position of the valve element 600, 650, 670 along the lead 200.

The transcatheter tricuspid prosthesis 602 is shown occupying the tricuspid orifice 104 after full expansion. The truncated cone shape allows a larger atrial orifice 608 than ventricular orifice 610 allowing low impingement on the right ventricle 114 while providing support for the tricuspid leaflets to avoid periprosthetic regurgitation. The shape also allows acceleration of blood flow preventing thrombus formation. The prosthesis anchor is tightened on the lead 200 after proper positioning and is steerable as described to change the angulation of the prosthesis towards the ventricular septum.

As has been discussed, the valve elements 600, 650, 670 are introduced along the lead, with the valve elements 600, 650, 670 being laterally displaced from the lead so that the valve elements 600, 650, 670 are next to the lead 200. In contrast, valve elements that are introduced centered on the lead, that is, surrounding the lead, have to deal with repeated impingement of valve elements on the lead itself. Such a center-positioned lead that extends through the middle of the valvular prosthetic hangs the valve from the lead. The tissue elements of the valvular prosthesis are therefore subjected to impingement on the rigid structure of the lead, which can result in damage to the leaflets of the valvular prosthesis and its eventual failure or damage. In contrast, the valvular elements of the present disclosure do not impinge during operation on the lead, and are therefore much less susceptible to damage and eventual failure due to the impingement onto hard material.

Embodiments of the present disclosure, therefore, provide a cardiac valve delivery system, comprising a myocardial attachment system introduced intravenously up to the right ventricle and implanted from right side of the ventricular septum through the septal myocardium with possible secondary attachment points on adjoining myocardium of the ventricular septum or right ventricle; a lead configured to be inserted through a venous system leading to the heart, with the lead having a distal (or close to distal) end at the myocardial attachment system and allowing positioning of the lead direction perpendicularly (or close to 90 degrees) to the myocardial attachment system; and a transcatheter prosthesis element configured to be delivered crimped using guidance along the lead, by a guiding system positioned on the outer rim of the transcatheter prosthesis. The prosthesis positioning in the tricuspid valve is secured by an anchoring element configured to fix the transcatheter prosthesis in place along the lead.

In other aspects, the myocardial attachment apparatus comprises a screw deployable at an angle of substantially 90 degrees from a longitudinal axis of the distal end. The myocardial attachment system may alternatively be comprised of hooks, rods or struts placed in the septal myocardium and or adjoining right ventricular myocardium.

The myocardial attachment system further comprises in other aspects a mesh (or hooks, rods or any other additional anchoring system deployable on the left side of the ventricular septum) deliverable from a distal end thereto, the mesh configured to anchor through heart tissue or by pressure on heart tissue.

In other aspects, the transcatheter prosthesis comprises a prosthesis mesh crimpable to contain a crimped valve element deliverable along the lead by a guiding system placed on the outer rim of the prosthesis.

The guiding and anchoring element of the prosthesis comprises in another aspect a central immobile element attached to the prosthesis mesh; and a pair of articulated semi-cylindrical wings movably coupled to the central immobile element, the pair of wings movable between a delivery position in which the wings do not engage the lead, and an anchoring position in which the wings are closed in embrace over the lead to anchor the transcatheter prosthesis to the lead. The guiding and anchoring element comprises alternatively a central immobile element attached to the prosthesis mesh and a loop attached to the prosthesis mesh and around the lead.

In other aspects, the prosthesis mesh is conical in shape when uncrimped, with a first opening at a ventricular opening, and a second opening, larger than the first opening, deployed to be intra-atrial at anchoring.

The transcatheter prosthesis may be configured to allow existing valvular tissue in the heart to rest on top of an external side of the prosthesis mesh.

In other aspects, the lead guiding and supporting the transcatheter prosthesis comprises an elastic element formed by springs, fluid or semisolid buffer or a loop of the lead to allow dampening of the forces pushing the prosthesis posteriorly during systole. Alternatively, the lead guiding and supporting the transcatheter prosthesis comprises a widened width in any part of its body to allow improved anchoring of the prosthesis to the lead.

In another embodiment, a transcatheter prosthesis includes a prosthesis mesh crimpable to contain a crimped valve element deliverable along a lead; and an anchoring element configured to fix the transcatheter prosthesis in place along the lead, wherein the transcatheter prosthesis is configurable to be delivered intravenously to a heart along a lead by the guiding and anchoring element.

The anchoring element further comprises in other aspects a central immobile element attached to the prosthesis mesh; a secondary element mobile and steerable; and a pair of articulated semi-cylindrical wings movably coupled to the central immobile element, the pair of wings movable between a delivery position in which the wings do not engage the lead, and an anchoring position in which the wings are closed in embrace over the lead to anchor the transcatheter prosthesis to the lead. This steerable guiding and anchoring system allows to direct the prosthesis towards a myocardial wall allowing optimization of the flow direction Having an anchor inside the heart is important for other devices. That anchor may be used for devices related to repair. That is, the lead is used to support something that will pull on the annulus or replace the valve, or a device that will be a spacer in a center of a valve where a leak may occur. The forces applied to a spacer in a center of a valve are very large, and are repeated with each beat of a heart. An ability to place a properly anchored device using the embodiments of the present disclosure is another advantage thereof.

While the present disclosure has herein mainly discussed tricuspid valve repair and/or replacement, it should be understood that additional valves may also be repaired or replaced with embodiments of the present disclosure with some modifications which will be evident to those of skill in the art, and without departing from the scope of the disclosure. For example, embodiments of the cardiac valve delivery system and transcatheter prosthesis may be used for repair and/or replacement of a mitral valve in a heart. In a mitral valve embodiment, the implantation pathway may differ.

Mitral valve repair/replacement is in one embodiment transceptal. That is, a mitral implantation of a valve attached to the ventricular septum is amenable to performance by the embodiments of the present disclosure. However, in such a procedure, a lead cannot be maneuvered from the superior vena cava to a transceptal piercing. Therefore, a needle is introduced via the inferior vena cava. The lead 200 is caught with the needle, which is used for a transceptal puncture, and attachment is made to the septum from the left atrium. The structure and operation of the transcatheter prosthesis and lead are amenable to such use without departing from the scope of the disclosure.

Still further, the implantation of an anchor such as described above on the left or right side of a heart for repair or treatment of mitral and/or tricuspid valves is also amenable to use with the embodiments of the present disclosure.

Moreover, the execution of the embodiments of the disclosure are also possible in a variety of variations of the examples shown here and aspects of the disclosure highlighted above.

What is claimed is:

1. A transcatheter delivery system, comprising:
   a supporting and guiding lead configured to be inserted through a venous system leading to a heart and attached to the heart, with the supporting and guiding lead having a distal end;
   a myocardial attachment system at the distal end of the supporting and guiding lead, the myocardial attachment system configured to be introduced intravenously with the supporting and guiding lead up to a right ventricle of the heart and implanted from a right side of the heart into a ventricular septum using an anchor; and
   a transcatheter prosthesis element configured to be delivered crimped using guidance along the supporting and guiding lead, the transcatheter prosthesis element having a guiding system positioned on the outer rim of the transcatheter prosthesis element, the guiding system configured to allow steering of the prosthesis;
   wherein the myocardial attachment system comprises a screw deployable at an angle of substantially 90 degrees from a longitudinal axis of the distal end;
   wherein the myocardial attachment system further comprises a mesh deliverable from a distal end thereto, the mesh configured to anchor through heart tissue or by pressure on heart tissue;
   wherein the transcatheter prosthesis comprises a prosthesis mesh crimpable to contain a crimped valve element deliverable along the supporting and guiding lead by the guiding system placed on the outer rim of the prosthesis;
   wherein the prosthesis mesh is conical in shape when uncrimped, with a first opening at a ventricular opening, and a second opening, larger than the first opening, deployed to be intra-atrial at anchoring.

2. The transcatheter delivery system of claim 1, wherein transcatheter prosthesis positioning is secured by an anchoring element configured to fix the transcatheter prosthesis in place along the supporting and guiding lead.

3. The transcatheter delivery system of claim 1, wherein the myocardial attachment system further comprises at least one of hooks, rods, scallops, and struts deployable on a left side of the ventricular septum.

4. The transcatheter delivery system of claim 1, wherein the supporting and guiding lead comprises a widened width along a part of its body to allow improved anchoring of the prosthesis to the supporting and guiding lead.

5. The transcatheter delivery system of claim 1, wherein the anchoring element further comprises:
   a central immobile element attached to the prosthesis mesh; and
   a secondary element which is mobile and steerable with respect to the central immobile element.

6. A transcatheter delivery system, comprising:
   a supporting and guiding lead configured to be inserted through a venous system leading to a heart and attached to the heart, with the supporting and guiding lead having a distal end;
   a myocardial attachment system at the distal end of the supporting and guiding lead, the myocardial attachment system configured to be introduced intravenously with the supporting and guiding lead up to a right ventricle of the heart and implanted from a right side of the heart into a ventricular septum using an anchor; and
   a transcatheter prosthesis element configured to be delivered crimped using guidance along the supporting and guiding lead, the transcatheter prosthesis element having a guiding system positioned on the outer rim of the transcatheter prosthesis element, the guiding system configured to allow steering of the prosthesis;
   wherein the transcatheter prosthesis comprises a prosthesis mesh crimpable to contain a crimped valve element deliverable along the supporting and guiding lead by the guiding system placed on the outer rim of the prosthesis; and
   wherein the guiding system of the prosthesis comprises:

a central immobile element attached to the prosthesis mesh; and a pair of articulated semi-cylindrical wings movably coupled to the central immobile element, the pair of wings movable between a delivery position in which the wings do not engage the supporting and guiding lead, and an anchoring position in which the wings are closed in embrace over the supporting and guiding lead to anchor the transcatheter prosthesis to the supporting and guiding lead.

7. The transcatheter delivery system of claim 6, wherein the supporting and guiding lead is positionable perpendicular to the myocardial attachment system.

8. The transcatheter delivery system of claim 6, wherein the myocardial attachment system comprises a screw deployable at an angle of substantially 90 degrees from a longitudinal axis of the distal end.

9. The transcatheter delivery system of claim 8, wherein the myocardial attachment system further comprises a mesh deliverable from a distal end thereto, the mesh configured to anchor through heart tissue or by pressure on heart tissue.

10. The transcatheter delivery system of claim 9, wherein the transcatheter prosthesis is configured to allow existing valvular tissue in the heart to rest on top of an external side of the prosthesis mesh.

11. A transcatheter delivery system, comprising:

a supporting and guiding lead configured to be inserted through a venous system leading to a heart and attached to the heart, with the supporting and guiding lead having a distal end;

a myocardial attachment system at the distal end of the supporting and guiding lead, the myocardial attachment system configured to be introduced intravenously with the supporting and guiding lead up to a right ventricle of the heart and implanted from a right side of the heart into a ventricular septum using an anchor; and a transcatheter prosthesis element configured to be delivered crimped using guidance along the supporting and guiding lead, the transcatheter prosthesis element having a guiding system positioned on the outer rim of the transcatheter prosthesis element, the guiding system configured to allow steering of the transcatheter prosthesis element with respect to the lead;

wherein the myocardial attachment system comprises a screw deployable at an angle of substantially 90 degrees from a longitudinal axis of the distal end;

wherein the myocardial attachment system further comprises a mesh deliverable from a distal end thereto, the mesh configured to anchor through heart tissue or by pressure on heart tissue;

wherein the transcatheter prosthesis comprises a prosthesis mesh crimpable to contain a crimped valve element deliverable along the supporting and guiding lead by the guiding system placed on the outer rim of the prosthesis; and wherein the guiding system comprises:

a central immobile element attached to the prosthesis mesh; and a ring attached to the prosthesis mesh and around the supporting and guiding lead.

12. The transcatheter delivery system of claim 11, wherein the myocardial attachment system includes a secondary attachment point on an adjoining myocardium of the ventricular septum.

13. The transcatheter delivery system of claim 11, wherein the myocardial attachment system includes a secondary attachment point on the left ventricle.

14. The transcatheter delivery system of claim 11, wherein the myocardial attachment system comprises at least one of hooks, rods or struts placed in the septal myocardium and/or adjoining left ventricular myocardium.

15. A transcatheter prosthesis, comprising:

a prosthesis mesh crimpable to contain a crimped valve element deliverable along a supporting and guiding lead; and an anchoring element configured to fix the transcatheter prosthesis in place on the supporting and guiding lead and to allow steering of the prosthesis, the anchoring element including a rotating anchor system configured to allow steering of the valve element with respect to the lead;

wherein the transcatheter prosthesis is configurable to be delivered intravenously to a heart along the supporting and guiding lead by the anchoring element;

wherein the anchoring element further comprises:

a central immobile element attached to the prosthesis mesh;

a secondary element which is mobile and steerable; and a pair of articulated semi-cylindrical wings movably coupled to the central immobile element, the pair of wings movable between a delivery position in which the wings do not engage the supporting and guiding lead, and an anchoring position in which the wings are closed in embrace over the supporting and guiding lead to anchor the transcatheter prosthesis to the supporting and guiding lead.

16. The transcatheter prosthesis of claim 15, wherein anchoring element allows direction of the prosthesis towards a myocardial wall allowing improvement of a flow direction.

* * * * *